United States Patent [19]

Hoffmann et al.

[11] 3,956,368

[45] May 11, 1976

[54] PROCESS FOR THE PRODUCTION OF GUANIDINE SALTS OF ALIPHATIC MERCAPTOSULPHONIC ACIDS

[75] Inventors: Helmut Hoffmann, Cologne; Carlhans Süling, Odenthal-Hahnenberg, both of Germany

[73] Assignee: Bayer Aktiengesellschaft, Leverkusen, Germany

[22] Filed: June 14, 1974

[21] Appl. No.: 479,440

[30] Foreign Application Priority Data

June 16, 1973 Germany............................ 2330817

[52] U.S. Cl...................... 260/501.14; 260/609 R; 260/564 R; 260/45.75; 260/45.95 N; 526/291; 526/297; 526/342

[51] Int. Cl.². ........................................ C07C 129/00

[58] Field of Search .............................. 260/501.14

[56] References Cited

UNITED STATES PATENTS 2,695,310   11/1954   Schramm et al. .................. 260/501

OTHER PUBLICATIONS

Schramm et al., "The Synthesis of Mercapto—Alkanesulfonic Acids," *J. Am. Chem. Soc.* 77, 6231 (1955).

*Primary Examiner*—James O. Thomas, Jr.
*Assistant Examiner*—G. T. Breitenstein
*Attorney, Agent, or Firm*—Plumley & Tyner

[57] ABSTRACT

The invention relates to a process for the production of guanidinium salts of aliphatic mercaptosulphonic acids by reacting S-isothiuronium betains with gaseous ammonia in an inert organic solvent.

2 Claims, No Drawings

PROCESS FOR THE PRODUCTION OF GUANIDINE SALTS OF ALIPHATIC MERCAPTOSULPHONIC ACIDS

This invention relates to a process for the production of the guanidine salts of aliphatic mercaptosulphonic acids.

It is known that the desired compounds of the present invention may be prepared from S-isothiuronium betains by saponification with ammonia.

Thus, for example, *J. Am. Chem. Soc.* 77, 6231 (1955) and U.S. Pat. No. 2,695,310, describe the reaction of the isothiuronium salt, 2-S-thiuroniuum ethane sulphonate at elevated temperatures in aqueous ammonia. According to these literature references, the required compounds are obtained in a high yield. However, this method is accompanied by the disadvantage that the high yield is related only to crude reaction products, which are contaminated in particular by disulphides. It is not possible to detect such admixtures by the results of the elementary analysis, but the useful properties of the reaction products are always deleteriously affected in a quite specific manner when used as stabilisers, for example, for chlorine-containing synthetic plastics materials or for filaments of acrylonitrile copolymers. The efficacy as a stabiliser is determined by the content of SH-groups, and consequently a high content of disulphides as secondary products reduces the efficiency of the stabiliser. Furthermore, the disulphides which are present as by-products are incompatible with the products which are to be stabilised and the finished articles have a lower degree of transparency.

The products of the reaction according to the literature references referred to previously contain ammonium salts as additional impurities; it is true that these salts raise the melting point of the product, but they also impair the effectiveness of the reaction products as a stabiliser.

It is therefore an object of this invention to improve the purity of guanidinium salts of aliphatic mercaptosulphonic acids.

It is a further object to improve the yield of the aforementioned products with respect to the processes of the prior art.

These objects are accomplished by reaction of S-isothiuronium betains with ammonia if the reaction is carried out with gaseous ammonia in an organic sovent which is inert with respect to ammonia.

Accordingly, the present invention relates to a process for the production of a guanidinium salt of an aliphatic mercaptosulphonic acid of the general formula

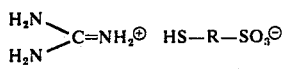

in which
R represents a saturated, straight chain or branched aliphatic radical, advantageously —$CH_2$—$CH_2$—, in a high yield and with improved purity, by reaction of S-isothiuronium betains with ammonia, wherein gaseous ammonia is introduced into a susupension of an S-isothiuronium betain in an organic solvent which is inert with respect to ammonia, at a temperature in the range of from 50° to 85°C, advantageously from 60° to 80°C.

As compared with the prior art, the compounds which are produced by the process according to the invention show a decidedly higher content of SH-groups, even without an additional purification being effected. The compounds which are less stable in the presence of atmospheric oxtgen are formed as white crystallisates, which are not discoloured on exposure to air, in contrast to the products obtained according to the previous methods, and which do not cause any turbidity in the finished articles when they are used as stabilising additives.

Suitable starting materials for the reaction according to the invention include any aliphatic S-isothiuronium betains, which can for example be obtained by reacting aliphatic sulphonic acids, which contain halogen, such as chlorine, bromine or iodine, as substituent, with any arbitrary thioureas. The constitution of the aliphatic radical is not critical and it is, for example, also possible to use aliphatic halogenated suphonic acids, which contain an ether bridge; since the resulting guanidinium salts can however be used as stabiisers, of which the efficacy is determined by the content of SH-groups, it is preferred to use low molecular weight S-isothiuronium betains as the starting material.

The reaction is generally carried out in such a way that an S-isothiuronium betain is suspended in an organic solvent, in which it is insoluble or is only sparingly soluble, and into which gaseous ammonia is introduced while stirring. The reaction temperature should be at least 50°C, but preferably higher than 60°C, in order to produce a useable high reaction speed. Reaction temperatures of 85°C (preferably 80°C) should not be exceeded, because otherwise the resulting products are not formed as white, crystalline powders, but as yellow-colored, crystalline products.

The choice of the solvent is not critical, if a reaction with the ammonia or with the S-isothiuronium betain is excluded, as for example with hydrocarbons, ethers, sterically hindered esters, amides, alcohols or with ketones. It is proved to be particularly desirable to use low aliphatic alcohols having 1 to 4 carbon atoms; advantageously isobutanol, isopropanol and ethanol are employed as solvents.

After a sufficient quantity of ammonia has been introduced into the reaction mixture, a clear solution forms, and the reaction product is separated out on cooling in crystalline form and with high purity.

Strict exclusion of water is unnecessary with the process according to the invention; particularly favourable results as regards the purity of the products are produced when the proportion of water in the reaction mixture does not exceed 10% by weight.

The following Examples are to further illustrate the invention without limiting it.

EXAMPLE 1

Guanidine-2-mercaptoethane sulphonate:

25 g of ammonia gas were introduced into 500 g of isobutanol until the pH value was in the range from 11 to 11.5. At 60° to 65°C and while stirring, 100 g of dry β-S-thiuronium ethane sulphonate were introduced in 4 batches, each of 25 g, and at intervals of 30 minutes each. With regular introduction of ammonia, the pH fell from 11 to 9.3. The reaction took place at 75° to 80°C.

After completing the introduction, the mixture was subsequently stirred with introduction of ammonia at 75° to 80°C. After 8 hours, a clear solution formed.

Ammonia consumption: 60 g.

The clear solution was then cooled over a period of 5 to 7 hours to 0°C; the crystal magma was filtered off with suction; the suction-filtered cake was covered twice with a little ethyl acetate and dried at 40° to 50°C under vacuum.

Yield: 100.5 g of dry, pure white crystals = 87.3% of the theoretical yield. Analysis: 19.6/19.7% N    93.8 mol% 201; SH    92.6 mol% 201; m.p: 114° to 117°C.

EXAMPLE 2

Guanidine-2-mercaptoethane sulphonate:

25 g of ammonia gas were introduced into 500 g of isobutanol until the pH value was in the range from 11 to 11.5. At 60°C and while stirring, 141 g of moist β-S-thiuronium ethane sulphonate were introduced in 4 equal proportions and at respective intervals of 30 minutes. With regular introduction of ammonia, the pH value fell from 11.5 to 9.3. The reaction was carried out at 70° to 80°C.

After the introduction, the batch was subsequently stirred at 70° to 80°C while introducing $NH_3$. After 5½ hours, a clear solution formed. Ammonia consumption: 35 g.

After the working-up operation, as described in Example 1, 125.5 g of pure white, dry crystals were obtained equivalent to 88% of the theoretical yield.

Analysis: 91.0% of SH mol 201; m.p: 110° to 112°C.

EXAMPLE 3

Guanidine-2-mercaptoethane sulphonate:

25 g of ammonia were introduced into 500 g of isopropanol and 120 g of moist β-S-thiuronium ethane sulphonate were added in the manner previously described. The reaction took place at 60° to 65°C; the pH value fell from 11 to 9. A clear solution was obtained after 4 hours. Consumption of ammonia during the reaction: 50 g.

After working up in the usual manner, 87 g of pure white dry crystals were obtained equivalent to 74.3% of the theoretical yield.

Analysis: 92.6% of SH mol 201 m.p: 110° to 113°C.

EXAMPLE 4

Guanidine-2-mercaptoethane sulphonate:

The reaction of 100 g of β-S-thiuronium ethane sulphonate in dry form in 500 g of isopropanol required 16 hours until the clear solution was obtained, at a reaction temperature from 65° to 67°C and with a total consumption of 170 g of ammonia gas. After working up in the usual manner, 100.5 g of pure white dry crystals were obtained.

Yield: 85.3% of the theoretical yield. Analysis: 92.0% SH; m.p: 110° to 114°C.

What we claim is:

1. A process for the production of a guanidinium salt of an alkyl mercaptosulphonic acid of the general formula:

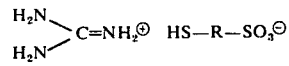

in which R represents —$CH_2CH_2$— in a high yield and with improved purity, which comprises reacting an S-isothiuronium betain with ammonia said reacting being effected by introducing gaseous ammonia into a suspension of said S-isothiuronium betain in an saturated aliphatic alcohol having 1 to 4 carbon atoms and which is inert with respect to ammonia, at a temperature in the range from 50° to 85°C.

2. The process of claim 1, wherein said temperature is from 60° to 80°C.

* * * * *